(12) United States Patent
Chevion et al.

(10) Patent No.: US 11,033,630 B2
(45) Date of Patent: Jun. 15, 2021

(54) METHOD AND PHARMACEUTICAL COMPOSITION FOR TREATMENT OF NEURODEGENERATION

(71) Applicants: Mordechai Chevion, Jerusalem (IL); Vladimir Vinokur, Beer Sheva (IL); Eduard Berenshtein, Jerusalem (IL)

(72) Inventors: Mordechai Chevion, Jerusalem (IL); Vladimir Vinokur, Beer Sheva (IL); Eduard Berenshtein, Jerusalem (IL)

(73) Assignees: Mordechai Chevion; Vladimir Vinokur; Eduard Berenshtein

( * ) Notice: Subject to any disclaimer, the term of this patent is extended or adjusted under 35 U.S.C. 154(b) by 0 days.

(21) Appl. No.: 16/074,291

(22) PCT Filed: Feb. 8, 2017

(86) PCT No.: PCT/IL2017/050159
§ 371 (c)(1),
(2) Date: Jul. 31, 2018

(87) PCT Pub. No.: WO2017/137988
PCT Pub. Date: Aug. 17, 2017

(65) Prior Publication Data
US 2019/0358334 A1 Nov. 28, 2019

Related U.S. Application Data

(60) Provisional application No. 62/293,803, filed on Feb. 11, 2016.

(51) Int. Cl.
*A61K 47/54* (2017.01)
*A61P 25/28* (2006.01)
(Continued)

(52) U.S. Cl.
CPC .......... *A61K 47/547* (2017.08); *A61K 9/0019* (2013.01); *A61K 33/24* (2013.01);
(Continued)

(58) Field of Classification Search
CPC .. A61K 47/547; A61K 33/242; A61K 33/244; A61K 9/0019; A61K 33/24;
(Continued)

(56) References Cited

U.S. PATENT DOCUMENTS

| 4,166,452 A | 9/1979 | Generales, Jr. |
| 4,256,108 A | 3/1981 | Theeuwes |

(Continued)

FOREIGN PATENT DOCUMENTS

WO  WO-2011021203 A2  2/2011

OTHER PUBLICATIONS

Liddell et al, Lipophilic adamantyl- or deferasirox-based conjugates of desferrioxamine B have enhanced neuroprotective capacity: implications for Parkinson disease, 2013, Free Radical Biology Medicine, 60, pp. 147-156. (Year: 2013).*

(Continued)

*Primary Examiner* — Trevor Love
(74) *Attorney, Agent, or Firm* — Harness, Dickey & Pierce, P.L.C.

(57) ABSTRACT

The present invention provides pharmaceutical compositions comprising a metal-desferrioxamine B complex or a combination thereof, for preventing, inhibiting, reducing or ameliorating neurodegeneration, thereby treating diseases, disorders, or conditions characterized by or associated with neurodegeneration; as well as methods of use.

5 Claims, 6 Drawing Sheets

(51) Int. Cl.
  A61K 33/242    (2019.01)
  A61K 33/244    (2019.01)
  A61K 9/00      (2006.01)
  A61K 33/24     (2019.01)
  A61K 33/30     (2006.01)
  A61P 43/00     (2006.01)
  A61P 25/16     (2006.01)
  A61P 25/14     (2006.01)
  A61P 25/00     (2006.01)
  A61K 33/00     (2006.01)
  A61K 31/164    (2006.01)
  A61K 31/28     (2006.01)
  A61K 31/315    (2006.01)

(52) U.S. Cl.
  CPC .......... *A61K 33/242* (2019.01); *A61K 33/244* (2019.01); *A61K 33/30* (2013.01); *A61P 25/28* (2018.01)

(58) Field of Classification Search
  CPC ...... A61K 33/30; A61K 33/00; A61K 31/164; A61K 31/28; A61K 31/315; A61P 25/28; A61P 43/00; A61P 25/16; A61P 25/14; A61P 25/00
  See application file for complete search history.

(56) References Cited

U.S. PATENT DOCUMENTS

| | | | | |
|---|---|---|---|---|
| 4,265,874 | A |   | 5/1981 | Bonsen et al. |
| 5,075,469 | A |   | 12/1991 | Chevion |
| 5,328,992 | A | * | 7/1994 | Peter ............... C08G 65/329 534/16 |
| 5,618,838 | A | * | 4/1997 | Chevion ............ A61K 33/30 514/492 |
| 8,975,294 | B2 |   | 3/2015 | Chevion et al. |
| 2004/0235864 | A1 | * | 11/2004 | Graczyk ............ A61P 11/06 514/259.1 |

OTHER PUBLICATIONS

Washington University School of Medicine, Surprising culprit in nerve cell damage identified, Mar. 24, 2017, Science Daily, pp. 1-5 (Year: 2017).*

International Search Report and Written Opinion of the International Searching Authority issued in PCT/IL2017/050159, dated May 14, 2017; ISA/Israel Patent Office.

Liddell, J. R. et al.: "Lipophilic adamantyl- or deferasirox-based conjugates of desferrioxamine B have enhanced neuroprotective capacity: implications for Parkinson disease", Free Radical Biology and Medicine, 60 (2013), pp. 147-156, Jan. 26, 2013 (Jan. 26, 2013).

Banin, E. et al.: "Injury Induced by Chemical Warfare Agents: Characterization and Treatment of Ocular Tissues Exposed to Nitrogen Mustard", Invest Opthalmol Vis Sci., vol. 44, No. 7, Jul. 2003, pp. 2966-2972.

Basso, D. M. et al.: "Basso Mouse Scale for Locomotion Detects Differences in Recovery after Spinal Cord Injury in Five Common Mouse Strains", Journal of Neurotrauma, vol. 23, No. 5, 2006, pp. 635-659.

Bibi, H., et. al.: "Zn/Ga-DFO iron-chelating complex attenuates the inflammatory Process in a mouse model of asthma", Redox Biology, 2, 2014, pp. 814-819.

Bittner, S. et. al.: "Myelin Oligodendrocyte Glycoprotein (MOG35-55) Induced Experimental Autoimmune Encephalomyelitis (EAE) in C57BL/6 Mice", Journal of Visualized Experiments, 86, Apr. 2014, pp. 1-5.

Chevion, M.: "A Site-Specific Mechanism for Free Radical Induced Biological Damage: The Essential Role of Redox-Active Transition Metals", Free Radical Biology & Medicine, 1988, vol. 5, (1) pp. 27-37.

Chevion, M.: "Protection Against Free Radical-Induced and Transition Metal-Mediated Damage: The Use of "Pull" and "Push" Mechanisms", Free Radic Res Commun., 1991, vols. 12-13. pp. 691-696.

Chevion, M., et al.: "Copper and iron are mobilized following myocardial ischemia: Possible predictive criteria for tissue injury", Proc. Natl. Acad. Sci. USA, vol. 90, (3), Feb. 1993, pp. 1102-1106.

Chevion, M., et al.: "The Role of Transition Metal Ions in Free Radical-Mediated Damage", *Reactive Oxygen Species in Biological Systems: An Interdisciplinary Approach*, Gilbert and Colton, (Eds.), Plenum Publishers, New York, 1999, pp. 103-131.

Connor, J. R. et al.: "Iron and Iron Management Proteins in Neurobiology", Pediatric Neurology, vol. 25, No. 2, 2001, pp. 118-129.

Faden, A. I. et al.: "Progressive inflammation-mediated neurodegeneration after traumatic brain or spinal cord injury", British Journal of Pharmacology, 2016, 173 (4), pp. 681-691.

Jackson-Lewis, V. et. al.: "Protocol for the MPTP mouse model of Parkinson's Disease", Nature Protocols, vol. 2, No. 1, 2007, pp. 141-151.

Kim, N. H. et al.: "Increased ferric iron content and iron-induced oxidative stress in the brains of scrapie-infected mice", Brain Research, No. 884, (1-2), 2000, pp. 98-103.

Kumar, V. et al.: "Aluminium neurotoxicity: neurobehavioural and oxidative aspects", Arch Toxicol. 83 (11), 2009, pp. 965-978.

Mantyh, P. W. et al.: "Aluminum, Iron, and Zinc Ions Promote aggregation of Physiological Concentrations of Beta-Amyloid Peptide", Journal of Neurochemistry, vol. 61, No. 3, 1993, pp. 1171-1174.

Morad, Y. et al.: "Treatment of Ocular Tissues Exposed to Nitrogen Mustard: Beneficial Effect of Zinc Desferrioxamine Combined with Steroids", Investigative Ophthalmology & Visual Science, vol. 46, No. 5, May 2005, pp. 1640-1646.

Orcutt, K. M. et al.: "A Lanthanide-Based Chemosensor for Bioavailable $Fe^{3+}$ Using a Fluorescent Siderophore: An Assay Displacement Approach", Sensors, 10 (2), 2010, pp. 1326-1337; doi:10.3390/s100201326.

Ravelli, K. G. et al.: "Intracerebroventricular Streptozotocin as a Model of Alzheimer's Disease: Neurochemical and Behavioral Characterization in Mice", Neurotox Res, 31, 2016, pp. 327-333, DOI 10.1007/s12640-016-9684-7.

Rouault, T.: "Iron metabolism in the CNS: implications for neurodegenerative diseases", Nature Reviews Neuroscience, vol. 14, Aug. 2013, pp. 551-564.

Scheiber, I. F. et al.: "Metabolism and functions of copper in brain", Progress in Neurobiology, 116, 2014, pp. 33-57.

Siganos, C. S. et al.: "Topical use of zinc desferrioxamine for corneal alkali injury in a rabbit model", Cornea, 17 (2), Mar. 1998, pp. 191-195.

Singh, N. et al.: "Iron in Neurodegenerative Disorders of Protein Misfolding: A Case of Prion Disorders and Parkinson's Disease", Antioxidants & Redox Signaling, vol. 21, No. 3, 2014, pp. 471-484, DOI: 10.1089/ars.2014.5874.

Sooriyaarachchi, M. et al.: "Removal of Fe3+ and Zn2+ from plasma metalloproteins by iron chelating therapeutics depicted with SEC-ICP-AES", Dalton Transactions, 39 (32), 2010, pp. 7466-7473.

Wan, W. et al.: "Applications of Induced Pluripotent Stem Cells in Studying the Neurodegenerative Diseases", Stem Cells International, vol. 2015, Article ID 382530, 2015.

Williams, T. L. et al.: "Europium as an inhibitor of Amyloid-β(1-42) induced membrane permeation", FEBS Lett., Oct. 24; 589(21), 2015: pp. 3228-3236.

Bellingham, Shayne A. et al., "The secret life of extracellular vesicles in metal homeostasis and neurodegeneration." Biology of the Cell, vol. 107, No. 11, pp. 389-418 (Nov. 2015).

Ciechanover, Aaron et al., "Protein Quality Control by Molecular Chaperones in Neurodegeneration." Frontiers in Neuroscience, vol. 11, No. 185, pp. 1-18 (Apr. 2017).

Di Giulio, A. M. et al., "Denervation and hyperinnervation in the nervous system of diabetic animals. II. Monoaminergic and peptidergic alterations in the diabetic encephalopathy." Journal of Neuroscience Research, vol. 24, No. 3, pp. 362-368 (Nov. 1989).

(56) References Cited

OTHER PUBLICATIONS

Dugger, Brittany N. et al., "Pathology of Neurodegenerative Diseases." Cold Spring Harbor Perspectives in Biology, vol. 9, No. 7, a028035, pp. 1-22 (Jul. 2017).
Ferik, Sevgi et al., "Diabetic polyneuropathy, deep white matter lesions, and carotid atherosclerosis: is there any association?" Neurological Sciences, vol. 39, pp. 103-110 (2018).
Grabrucker, Andreas M. et al., "Brain-Delivery of Zinc-Ions as Potential Treatment for Neurological Diseases: Mini Review." Drug Delivery Letters, vol. 1, No. 1, pp. 13-23 (2011).
Jolivalt, Corinne G. et al., "Similar pattern of peripheral neuropathy in mouse models of type 1 diabetes and Alzheimer's disease." Neuroscience, vol. 202, pp. 405-412 (Jan. 27, 2012).
Karck, Matthias et al., "The push-and-pull mechanism to scavenge redox-active transition metals: A novel concept in myocardial protection." Journal of Thoracic and Cardiovascular Surgery, vol. 121, No. 6, pp. 1169-1178 (Jun. 2001).
Massie, Rami et al., "Diabetic cervical radiculoplexus neuropathy: a distinct syndrome expanding the spectrum of diabetic radiculoplexus neuropathies." Brain, vol. 135, No. 10, pp. 3074-3088 (Oct. 2012).
Messier, Claude, "Diabetes, Alzheimer's disease and apolipoprotein genotype." Experimental Gerontology, vol. 38, No. 9, pp. 941-946 (Sep. 2003).
Morris, Deborah R. et al., "Neurotoxicity of Zinc." Neurotoxicity of Metals, Advances in Neurobiology, vol. 18, pp. 303-312 (2017).
Park, Moon Ho et al., "Vascular risk factors and the effect of white matter lesions on extrapyramidal signs in Alzheimer's disease." International Psychogeriatrics, vol. 23, No. 5, pp. 780-787 (2011).
Pochwat, Bartlomiej et al., "Relationship between Zinc (Zn2+) and Glutamate Receptors in the Processes Underlying Neurodegeneration." Neural Plasticity, vol. 2015, No. 591563, pp. 1-9 (2015).
Summers, Paul E. et al., "Spinal Cord fMRI." Quantitative MRI of the Spinal Cord, Academic Press, pp. 221-239 (2014).
Szewczyk, Bernadeta, "Zinc homeostasis and neurodegenerative disorders." Frontiers in Aging Neuroscience, vol. 5, No. 33, pp. 1-12 (Jul. 2013).
Tabrizi, S., "Neurodegenerative diseases neurobiology pathogenesis and therapeutics." Journal of Neurology, Neurosurgery & Psychiatry, vol. 77, No. 2, p. 284 (Feb. 2006).
Ward, R. E. et al., "A characterization of white matter pathology following spinal cord compression injury in the rat." Neuroscience, vol. 260, pp. 227-239 (Feb. 28, 2014).
Yagihashi, Soroku et al., "Mechanism of diabetic neuropathy: Where are we now and where to go?" Journal of Diabetes Investigation, vol. 2, No. 1, pp. 18-32 (Feb. 2011).
Yaguchi, Masamitsu et al., "Neuropathological study of C57BL/6Akita mouse, type 2 diabetic model: Enhanced expression of αβ-crystallin in oligodendrocytes." Neuropathology, vol. 23, No. 1, pp. 44-50 (Mar. 2003).

* cited by examiner

ID
METHOD AND PHARMACEUTICAL COMPOSITION FOR TREATMENT OF NEURODEGENERATION

CROSS REFERENCE TO RELATED APPLICATIONS

This application is a U.S. National Phase Application under 35 U.S.C. 371 of International Application No. PCT/IL2017/050159 filed on Feb. 8, 2017 and published in English as WO 2017/137988 A1 on Aug. 17, 2017. This application claims priority to U.S. Provisional Application No. 62/293,803 filed on Feb. 11, 2016. The entire disclosures of all of the above applications are incorporated herein by reference.

TECHNICAL FIELD

The present invention relates to methods and compositions for treatment of acute or chronic pathologic conditions characterized by neurodegeneration.

BACKGROUND ART

Neurodegeneration is an umbrella term for a group of pathologies associated with progressive loss of brain tissue structure and/or decrease in the function of neurons, including death. Examples of such pathologies of the nervous system include Parkinson's disease, Alzheimer's disease, Huntington's disease, advanced age related brain degeneration, Creutzfeldt-Jakob disease and amyotrophic lateral sclerosis, all resulting from a neurodegenerative process. Currently, such neurodegenerative diseases are considered incurable, and result in progressive degeneration and/or death of neuronal cells. Additionally, the mechanisms of neurodegeneration were reported to play a crucial role in the pathophysiology of spinal cord and brain injury of various etiologies, stroke, vascular dementia, and neurotoxicity induced by a variety of agents (Wan et al., 2015; Faden et al., 2016).

Iron, an abundant metallic-element in mammals in general and in humans in particular, is an essential element for life that plays key roles in biological systems. In healthy adults, the total amount of iron is 3-4 grams, wherein some of this iron is bound to iron-containing enzymes, redox and storage of iron proteins including proteins involved in cellular respiration and electron transport. On the other hand, the "labile" iron pool, where iron is redox-active, represents a minute amount of iron in transition or in transport, which serves as a catalyst for the production of reactive oxygen-derived species (ROS), including the hydroxyl radicals via the Fenton reaction. ROS generate oxidative stress that leads to tissue injury. Many publications connect excess tissue (labile redox-active) iron with ROS-induced tissue damage, in a large number of pathologic phenomena, and in different organs and tissues including the central and the peripheral nervous systems.

A growing volume of evidence demonstrates a relationship between abnormalities of iron metabolism and/or excessive accumulation of iron in certain regions of the brain, and neurodegenerative processes. This liaison has been reported for amyotrophic lateral sclerosis, Parkinson's disease, Alzheimer's disease, stroke, and spinal cord injury, Friedreich's ataxia, brain injury, types of intoxication and several other pathologies (Connor et al., 2001; Rouault. 2013). Similar arguments can be stated about aluminum, and to a lesser extent for copper (Kumar and Gill, 2009; Scheiber et al., 2014). Some attempts have been made to apply different iron-sequestering compounds in treating those pathologies in preclinical models; however, the main drawback of the iron chelators currently available is their low ability to penetrate the cellular membranes, and more importantly, to cross the blood-brain barrier. In addition, their administration is associated with negative side effects and toxicities. In the absence of excess of iron, the iron chelators can interfere with the homeostasis of copper, zinc and other metal micronutrients. The stability constants of the complexes of these iron chelators with other metal ions are markedly smaller compared to the complex with $Fe^{3+}$.

A special role of iron was reported in regard to diseases caused by prions, i.e., infectious agents composed entirely of protein material called PrP (prion protein). PrP can fold in multiple structurally distinct ways, at least one of which is transmissible to other prion proteins, forming extremely stable aggregates, causing tissue damage and cell death. Prions cause a neurodegenerative disease by aggregating extracellularly within the central nervous system to form amyloid plaques, which disrupt normal brain tissue. This disruption is characterized by "holes" in the tissue with resultant spongy architecture due to the vacuole formation in the neurons. According to some reports, redox-active iron generating ROS through the Fenton reaction contributes as a result to PrP misfolding (Singh et al., 2014; Kim et al., 2000). Diseases caused by prions include Creutzfeldt-Jakob disease (CJD) and its subtypes such as iatrogenic CJD (iCJD), variant CJD (vCJD) and sporadic CJD (sCJD), Gerstmann-Sträussler-Scheinker syndrome, fatal familial insomnia, kuru, Familial spongiform encephalopathy, and multiple system atrophy. The formation of amyloid plaques is a common feature in pathophysiology of prions diseases, Alzheimer's disease, and Parkinson's disease. The proteins featured in process of the formation of the plaque vary from disease to disease, e.g. β-amyloid (Aβ) in Alzheimer's disease, or α-synuclein in Parkinson's disease.

Zinc-desferrioxamine B (Zn-DFO) and gallium-desferrioxamine B (Ga-DFO) are metal complexes, previously shown to inhibit the catalysis by iron (and copper) during ROS formation. Their protective activity can be visualized through the chelation—"pulling" out and sequestering the available and redox-active iron, which is responsible for injury. In addition to the chelation of iron by the DFO component of these complexes, the metal component (a relatively inert zinc or gallium ion) is liberated during the exchange of iron within the complex, and further acts as a secondary antioxidant by "pushing" out additional iron ions from their binding sites (Chevion, 1988; Chevion, 1991). The spatial structures of these complexes are markedly different from that of DFO per se, allowing for enhanced infiltration of the complexes into cells (Chevion, 1991).

As previously shown, treatment with Zn-DFO and/or Ga-DFO yielded a potent beneficial effect in animal models of human skin and corneal damage, asthma, diabetes, inflammatory bowel disease (IBD) and cataract formation (Siganos et al., 1998; Bibi et al., 2014; U.S. Pat. No. 8,975,294). In addition, topical administration of said metal-DFO complexes was found to be effective in alleviating the symptoms of exposure to the chemical warfare agent mustard, more particularly nitrogen mustard (Banin et al., 2003; Morad et al., 2005).

The toxicity of Aβ oligomers may arise from their ability to interact with and disrupt cellular membranes, promoting the misfolding of Aβ plaques formation in the cell. This process is mediated by GM1 ganglioside receptors within these membranes. Therefore, inhibition of Aβ-membrane interactions could provide means of preventing the toxicity associated with Aβ. Europium ($Eu^{3+}$) was reported to bind to the GM1-containing membranes and prevent the interaction with Aβ in a cell culture. Thus, the process of propagation of plaques can be arrested (Williams et al., 2015). The similar feature, though to a lesser extent, was demonstrated by ions of the lanthanides, e.g., $Er^{3+}$, $Gd^{3+}$, $La^{3+}$, and $Yb^{3+}$. Yet, the ability of these ions to cross the blood-brain barrier is very limited, inter alia, due to their charge.

SUMMARY OF INVENTION

In order for a drug to be considered a candidate for treating neurodegeneration, said drug should first show efficacy in providing specific benefits to injured brain cells, such as ameliorating inflammatory responses and/or inhibiting the aggregation of amyloid molecules or synuclein. This condition can be shown even in a brain cell culture. Yet, in order to be considered a candidate for a successful treatment of neurodegeneration, said drug should meet a further essential condition, i.e., should be able to effectively infiltrate into the brain by crossing, e.g., the blood-brain barrier or the blood-CSF barrier.

It has now been found, in accordance with the present invention, that metal-DFO complexes such as Zn-DFO complex are capable of infiltrating into the brain remarkably better than DFO alone. An additional indirect evidence for the infiltrability of the Zn-DFO complex through the blood-cerebrospinal fluid (CSF) barrier has been obtained in a further study exemplified herein, showing the beneficial effects of the Zn-DFO complex on the healing of spinal cord from a mechanical trauma, as clearly demonstrated by both physiological parameters and structural aspects of the spinal cord. In other words, the studies exemplified herein show that metal-DFO complexes, e.g., Zn-DFO complex, are highly effective in diminishing the rate of a neurodegenerative process, i.e., inhibiting, reducing or ameliorating neurodegeneration, thus capable of treating medical conditions associated with, or characterized by, a neurodegenerative process.

In this respect, it should be emphasized that the ferric Fe-DFO complex, resulting from the exchange of, e.g., zinc of Zn-DFO or gallium of Ga-DFO, by tissue-borne iron, is an inert complex where the iron does not redox cycle, which is entirely excreted out of the body.

In one aspect, the present invention thus relates to a method for preventing, inhibiting, reducing or ameliorating neurodegeneration, thus more particularly treating a disease, disorder or condition characterized by or associated with neurodegeneration, in a subject in need thereof, comprising administering to said subject a therapeutically effective amount of at least one metal-DFO complex, e.g., Zn-DFO complex, or a combination thereof.

The neurodegeneration prevented, inhibited, reduced or ameliorated by the method of the present invention may be associated with a neurodegenerative disease, disorder or condition such as Parkinson's disease, Alzheimer's disease, amyotrophic lateral sclerosis, Huntington's disease, or age-related brain degeneration; a disorder or condition induced by, or resulting from, an injury caused by, e.g., a mechanical force, ischemia, a toxic agent, or hemorrhage; or a disease, disorder or condition caused by prion, such as Creutzfeldt-Jakob disease or a subtype thereof, fatal familial insomnia, kuru, Familial spongiform encephalopathy, or multiple system atrophy.

In another aspect, the present invention provides a pharmaceutical composition for preventing, inhibiting, reducing or ameliorating neurodegeneration, thus more particularly treating a condition characterized by or associated with neurodegeneration, comprising at least one metal-DFO complex, e.g., Zn-DFO complex, or a combination thereof, and a pharmaceutically acceptable carrier.

In still another aspect, the present invention relates to a metal-DFO complex, e.g., Zn-DFO complex, or a combination thereof, for use in preventing, inhibiting, reducing, or ameliorating neurodegeneration.

In yet another aspect, the present invention relates to use of a metal-DFO complex, e.g., Zn-DFO complex, or a combination thereof, in the preparation of a pharmaceutical composition for preventing, inhibiting, reducing, or ameliorating neurodegeneration.

In a further aspect, the present invention provides a kit comprising (i) a first pharmaceutical composition comprising DFO or a pharmaceutically acceptable salt thereof; (ii) a second pharmaceutical composition comprising ions of at least one metal; and (iii) instructions to administer said compositions, either concomitantly or sequentially at any order and within a time period not exceeding 6 hours, so as to obtain in situ a complex of said DFO and said at least one metal to thereby prevent, inhibit, reduce, or ameliorate neurodegeneration, thus more particularly treat a condition characterized by or associated with neurodegeneration.

DETAILED DESCRIPTION

Figure 1A:
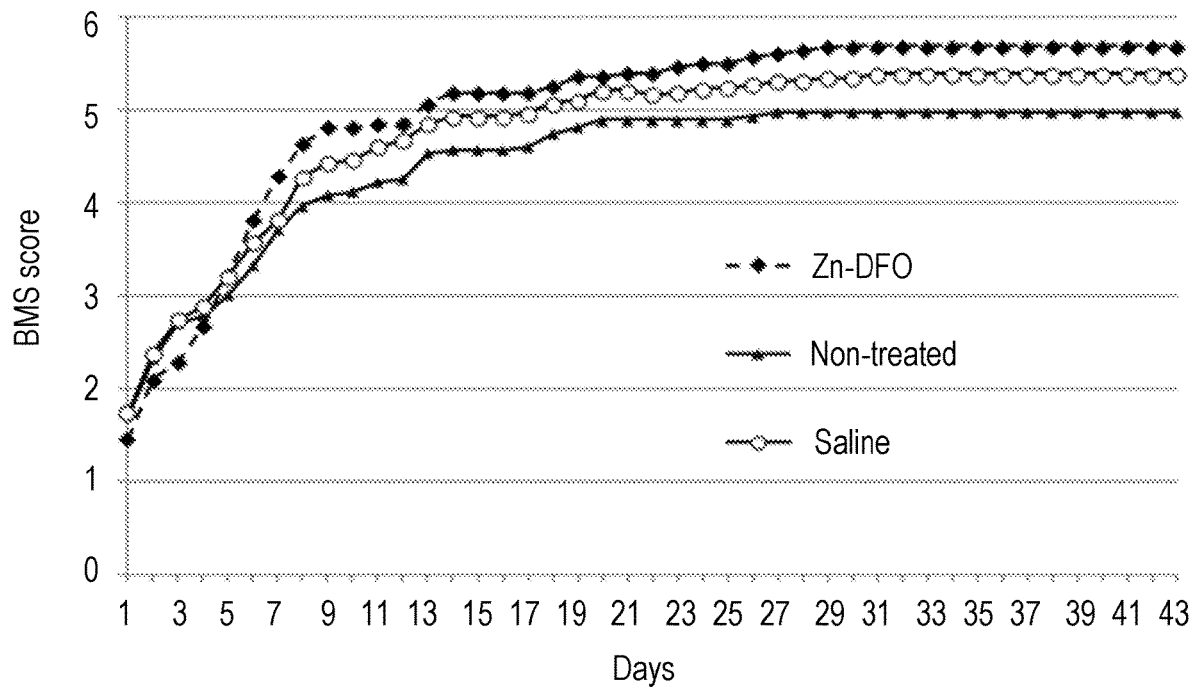
FIGS. 1A-1B show recovery from spinal cord injury in mice treated with Zn-DFO—BMS score (1A); and normalized BMS score that is based on the initial value taken as 100% (1B). Values are shown as averages.

In one aspect, the present invention relates to a method for preventing, inhibiting, reducing or ameliorating neurodegeneration, thus more particularly treatment of a disease, disorder or condition characterized by or associated with neurodegeneration, in a subject in need thereof, comprising administering to said subject a therapeutically effective amount of at least one, i.e., one, two, three or more, metal-DFO complex.

Without being bound by any theory, it is postulated that the protective effect of metal-DFO complexes results from several reasons including the suppressed formation of ROS. The ability of the metal-DFO complex to act via a combined "push-pull" mechanism to achieve such a marked reduction in free radical formation is supported by both theoretical considerations and previously reported experimental findings. In the Fenton reaction or in the metal-mediated Haber-Weiss mechanism, the conversion of low reactive species to the highly reactive hydroxyl radicals apparently depends on the availability of trace amounts of redox-active and labile iron or copper ions, which serve as essential catalysts in ROS formation (Chevion, 1988; Chevion et al., 1993; Chevion et al., 1998). It is thus hypothesized that said complexes, particularly Zn-DFO and Ga-DFO, exert their protective effect by intervening in this critical step of hydroxyl radical formation. Another possible mechanism of protection of the brain, in particular of the neurons, is the removal of iron, which is incriminated in accelerating the aggregation of β-amyloids (Mantyh et al., 1993).

It is postulated that some of the useful effects exerted by DFO in inhibiting ROS formation are achieved through its actions as a chelating agent (chelant, chelator, or sequestering agent), capable of forming soluble complexes, i.e., chelates, with certain metal ions and consequently inactivating said metal ions such that they cannot normally react with other elements or ions. Such chelates often have chemical and biological properties that are markedly different from those of either the chelator or metal ion, alone. For example, whereas DFO is a molecule having a noodle-like structure that can sparingly infiltrate into cells, metal-chelates formed by said molecule, e.g., the zinc-, gallium- or iron-chelates, assume a globular structure capable of infiltrating into cells. In recent experiments comparing the ability of DFO and Zn-DFO complex to penetrate cellular membranes in a tissue culture model, using H9C2 cardiomyocytes, it has been found that the ability of Zn-DFO to infiltrate into the cells is more than threefold higher than that of DFO alone (data not shown).

The terms "DFO", "desferrioxamine", "desferrioxamine B", "deferoxamine" or "Desferal®", as used herein interchangeably refer to the compound N'-[5-(Acetyl-hydroxyamino)pentyl]-N-[5-[3-(5-aminopentyl-hydroxy-carbamoyl)propanoylamino]pentyl]-N-hydroxy-butane diamide, a bacterial siderophore produced by the actinobacter *Streptomyces pilosus* (generally recognized as a safe organism). Desferal® is an iron chelating compound made up from six basic units that is marketed in the form of its mesylate salt. When not bound to a metal, DFO is a linear (noodle-like) molecule that cannot easily penetrate into most cells; however, upon metal binding it forms a globular complex. In addition to iron, DFO forms tight complexes with zinc. Based on the similarity of the ligand chemistry between iron or copper to zinc, it is assumed that the structure of zinc-DFO complex is also spherical rather than linear. Metal binding to the negatively charged DFO renders the molecule less polar. These considerations might explain why the DFO complexes more easily penetrate through cellular membranes and biological barriers, and more effectively bind intracellular metals that are redox active and mediate tissue damage. In this process, two steps provide antioxidant protection: a) the removal of redox-active iron and copper by their chelation, and b) the controlled release of zinc, that in itself possesses anti-oxidant activity and is needed for the adequate functioning of various metal enzymes.

The relative stability constants for the DFO complexes with Fe(III), Cu(II), Zn(II) and Ga(III) are $10^{31}$, $10^{14}$, $10^{11}$ and $10^{28}$, respectively. Based on these thermodynamic properties, upon penetration into cells, with high abundance of low molecular weight and redox-active complexes of Fe or Cu, the Zn-DFO complex exchanges the Zn with Fe or Cu, and the zinc released from the complex could have additional beneficial anti-oxidant and/or other effects. It should be noted that the stability constant of DFO complex with any of lanthanide ions is expected to be less than $10^{31}$ (Orcutt et al., 2010).

The term "subject" as used herein with respect to the method of the present invention refers to any mammal, e.g., a human.

The term "therapeutically effective amount" as used herein with respect to the metal-DFO complex(es) administered according to the method of the invention refers to an amount of said complex(es) that, upon administration under a particular regimen during a particular period of time, e.g., days, weeks or months, is sufficient to prevent, inhibit, reduce or ameliorate a neurodegenerative process occurring in the body of the subject administered with. The actual dosage of the metal-DFO complex(es) administered may be varied so as to obtain an amount of said metal-DFO complex(es) that is effective to achieve the desired prophylactic/therapeutic response for a particular subject and mode of administration, without being toxic to the subject. The dosage level selected will depend upon a variety of factors including the severity/progression of the disease, disorder or condition treated; the specific metal-DFO complex(es) employed, the administration route, and the duration of the treatment; drugs, if any, used in combination with the metal-DFO complex(es) employed; and the age, sex and weight of the subject treated. In general, it may be presumed that for preventive treatment lower doses will be needed, while higher doses will be required for treatment of subjects already showing pathological phenotypes of said neurodegeneration.

In certain embodiments, the metal-DFO complex administered according to the method of the present invention each independently is zinc-DFO complex, gallium-DFO complex, manganese-DFO complex, indium-DFO complex, silver-DFO complex, cobalt-DFO complex, gold-DFO complex, or a lanthanide-DFO complex. Particular lanthanides include lanthanum, cerium, praseodymium, neodymium, promethium, samarium, europium, gadolinium, terbium, dysprosium, holmium, erbium, thulium, ytterbium and lutetium. According to the invention, in cases wherein a combination of metal-DFO complexes is administered, said combination may comprise said metal-DFO complexes in any quantitative ratio. For example, in case a combination of two metal-DFO complexes is administered, said combination may comprise said two metal-DFO complexes in a quantitative ratio of about 100:1 to about 1:100, e.g., in a quantitative ratio of about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100. Similarly, in case a combination of three metal-DFO complexes is administered, said combination may comprise said three metal-DFO complexes in a quantitative ratio of, e.g., about 1:1:1, about 1:2:3, about 1:10:50, about 1:20:50, about 1:10:100, or about 1:50:100.

In particular embodiments, the metal-DFO complex administered according to the method of the invention is Zn-DFO complex, Ga-DFO complex, Eu-DFO complex, Gd-DFO complex, or a combination thereof, i.e., a combination of Zn-DFO complex and Ga-DFO complex; Zn-DFO complex and Eu-DFO complex; Zn-DFO complex and Gd-DFO complex; Ga-DFO complex and Eu-DFO complex; Ga-DFO complex and Eu-DFO complex; Eu-DFO complex and Gd-DFO complex; Zn-DFO complex, Ga-DFO complex and Eu-DFO complex; Zn-DFO complex, Ga-DFO complex and Gd-DFO complex; Zn-DFO complex, Eu-DFO complex and Gd-DFO complex; or Ga-DFO complex, Eu-DFO complex and Eu-DFO complex. In more particular such embodiments, a combination of both Zn-DFO complex and Ga-DFO complex is administered, e.g., such a combination wherein the quantitative ratio of the Zn-DFO complex to the Ga-DFO complex is in a range of about 100:1 to about 1:100, e.g., about 20:1 to about 1:20, about 10:1 to about 1:10, about 4:1 to about 1:4, about 3:1 to about 1:3, about 2:1 to about 1:2, or about 1:1. Certain such combinations are those wherein the amount of the Zn-DFO complex is higher than that of the Ga-DFO complex, e.g., combinations wherein the quantitative ratio of the Zn-DFO complex to the Ga-DFO complex is in a range of about 10:1 to about 2:1, e.g., about 10:1, about 9:1, about 8:1, about 7:1, about 6:1, about 5:1, about 4:1, about 3:1, or about 2:1.

In certain embodiments, the method of the present invention comprises administration of a combination of three or more metal-DFO complexes, e.g., a combination of Zn-DFO complex and Ga-DFO complex as defined above, together with one or more additional metal-DFO complexes such as, e.g., Eu-DFO complex or Gd-DFO complex.

The method of the present invention, according to any one of the embodiments defined above, is aimed at preventing, inhibiting, reducing or ameliorating neurodegeneration, thus in fact treating a disease, disorder or condition characterized by, or associated with, said neurodegeneration. In certain embodiments, the disease, disorder or condition characterized by, or associated with, neurodegeneration is a neurodegenerative disease, disorder or condition such as, without limiting, Parkinson's disease, Alzheimer's disease, amyotrophic lateral sclerosis, Huntington's disease, or age-related brain degeneration. In other embodiments, the disorder or condition characterized by, or associated with, neurodegeneration is a disorder or condition induced by, or resulting from, an injury, more particularly spinal cord- or brain-injury of various etiologies, e.g., an injury caused by a mechanical force, ischemia, a toxic agent, or hemorrhage. In further embodiments, the disease, disorder or condition characterized by, or associated with, neurodegeneration is a disease, disorder or condition caused by prion such as, without being limited to, Creutzfeldt-Jakob disease (CJD) or a subtype thereof such as iatrogenic CJD (iCJD), variant CJD (vCJD) and sporadic CJD (sCJD), Gerstmann-Sträussler-Scheinker syndrome, fatal familial insomnia, kuru, Familial spongiform encephalopathy, or multiple system atrophy.

In another aspect, the present invention provides a pharmaceutical composition for preventing, inhibiting, reducing or ameliorating neurodegeneration, thus more particularly treating a disease, disorder or condition characterized by or associated with neurodegeneration, said composition comprising at least one metal-DFO complex, herein also referred to as "the active agent(s)", and a pharmaceutically acceptable carrier.

In certain embodiments, the metal-DFO complex comprised within the pharmaceutical composition of the present invention each independently is zinc-DFO complex, gallium-DFO complex, manganese-DFO complex, indium-DFO complex, silver-DFO complex, cobalt-DFO complex, gold-DFO complex, or a lanthanide-DFO complex as defined above including, but not limited to, europium-DFO complex and gadolinium-DFO complex. According to the invention, the pharmaceutical composition disclosed may comprise, as the active agents, a combination of more than one, e.g., two or three, metal-DFO complexes in any quantitative ratio. For example, a composition comprising a combination of two metal-DFO complexes may contain said two metal-DFO complexes in a quantitative ratio of about 100:1 to about 1:100, e.g., in a quantitative ratio of about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100. Similarly, in case a combination of three metal-DFO complexes is administered, said combination may comprise said three metal-DFO complexes in a quantitative ratio of, e.g., about 1:1:1, about 1:2:3, about 1:10:50, about 1:20:50, about 1:10:100, or about 1:50:100.

In particular embodiments, the metal-DFO complex comprised within the pharmaceutical composition of the invention is Zn-DFO complex, Ga-DFO complex, Eu-DFO complex, Gd-DFO complex, or a combination thereof, i.e., a combination of Zn-DFO complex and Ga-DFO complex; Zn-DFO complex and Eu-DFO complex; Zn-DFO complex and Gd-DFO complex; Ga-DFO complex and Eu-DFO complex; Ga-DFO complex and Eu-DFO complex; Eu-DFO complex and Gd-DFO complex; Zn-DFO complex, Ga-DFO complex and Eu-DFO complex; Zn-DFO complex, Ga-DFO complex and Gd-DFO complex; Zn-DFO complex, Eu-DFO complex and Gd-DFO complex; or Ga-DFO complex, Eu-DFO complex and Eu-DFO complex. In more particular such embodiments, said composition comprises a combination of both Zn-DFO complex and Ga-DFO complex, e.g., wherein the quantitative ratio of the Zn-DFO complex to the Ga-DFO complex is in a range of about 100:1 to about 1:100, e.g., about 20:1 to about 1:20, about 10:1 to about 1:10, about 4:1 to about 1:4, about 3:1 to about 1:3, about 2:1 to about 1:2, or about 1:1. Certain such compositions are those wherein the amount of the Zn-DFO complex is higher than that of the Ga-DFO complex, e.g., wherein the quantitative ratio of the Zn-DFO complex to the Ga-DFO complex in the composition is in a range of about 10:1 to about 2:1, e.g., about 10:1, about 9:1, about 8:1, about 7:1, about 6:1, about 5:1, about 4:1, about 3:1, or about 2:1.

In certain embodiments, the pharmaceutical composition of the present invention comprises, as the active agents, a combination of three or more metal-DFO complexes, e.g., a combination of Zn-DFO complex and Ga-DFO complex as defined above, together with one or more additional metal-DFO complexes such as, e.g., Eu-DFO complex or Gd-DFO complex.

The pharmaceutical compositions of the present invention may be prepared by conventional techniques, e.g., as described in Remington: The Science and Practice of Pharmacy, 19$^{th}$ Ed., 1995. The compositions can be prepared, e.g., by uniformly and intimately bringing the active agent, i.e., the metal-DFO complex(es), into association with a liquid carrier, a finely divided solid carrier, or both, and then, if necessary, shaping the product into the desired formulation. The active agent may be applied as is, or conjugated to one or more pharmaceutically acceptable groups such as sugars, starches, amino acids, polyethylene-glycol (PEG), polyglycerol-based compounds, hydrazines, hydroxylamines, amines, or halides. The compositions may be in liquid, solid or semisolid form and may further include pharmaceutically acceptable fillers, carriers, diluents or adjuvants, and other inert ingredients and excipients. Each one of the inert ingredients should be both pharmaceutically and physiologically acceptable, i.e., both compatible with the other ingredients and not injurious to the subject. In one embodiment, the pharmaceutical composition of the invention is formulated as nanoparticles or microparticles.

The compositions contemplated herein can be formulated for any suitable route of administration, e.g., intravenous, intraarterial, intramuscular, intraperitoneal, intrathecal, epidural, intracerebral, intracerebroventricular, intrapleural, intratracheal or subcutaneous administration; oral administration; rectal administration; nasal administration; or inhalation. The dosages will depend on the state of the patient, and will be determined, from time to time, as deemed appropriate by the practitioner. For example, a physician or veterinarian could start doses of the active agent(s) employed in the pharmaceutical composition at levels lower than required in order to achieve the desired therapeutic effect, and gradually increase the dosage until the desired effect is achieved. Some administration routes, e.g., intraperitoneal or rectal, can be intended for treatment of intestinal malfunction linked to neurodegenerative diseases.

The pharmaceutical compositions of the invention may be administered, e.g., continuously, daily, twice daily, thrice daily or four times daily, for various duration periods, e.g., weeks, months, years, or decades.

The pharmaceutical composition of the invention may be in the form of a sterile injectable preparation, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution and isotonic sodium chloride solution.

Pharmaceutical compositions according to the invention, when formulated for administration route other than parenteral administration, may be in a form suitable for oral use, e.g., as tablets, troches, lozenges, or aqueous suspensions, dispersible powders or granules, emulsions, hard or soft capsules, or syrups or elixirs. Compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent(s) in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents. The tablets may be either uncoated or coated utilizing known techniques to delay disintegration and absorption in the gastrointestinal tract and thereby provide a sustained action over a longer period. For example, a time delay material may be employed. They may also be coated using the techniques described in the U.S. Pat. Nos. 4,256,108, 4,166,452 and 4,265,874 to form osmotic therapeutic tablets for control release.

Pharmaceutical compositions according to the invention, when formulated for inhalation, may be administered utilizing any suitable device known in the art, such as aerosol-base metered dose inhalers (MDIs), liquid nebulizers, dry powder inhalers (dispersion devices), sprayers, thermal vaporizers, electrohydrodynamic aerosolizers, and the like.

The pharmaceutical compositions of the invention may be formulated for controlled release of the active agent. Such compositions may be formulated as controlled-release matrix, e.g., as controlled-release matrix tablets in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Other contemplated formulations are depot systems, based on biodegradable polymers, wherein as the polymer degrades, the active agent is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

The pharmaceutical compositions of the present invention, as defined in any one of the embodiments above, are useful in preventing, inhibiting, reducing or ameliorating neurodegeneration, and therefore in treating a disease, disorder or condition characterized by, or associated with, said neurodegeneration. The disease, disorder or condition treatable by the pharmaceutical composition of the invention is any disease, disorder or condition characterized by, or associated with, neurodegeneration, such as a neurodegenerative disease, disorder or condition; a disorder or condition induced by, or resulting from, an injury, more particularly spinal cord- or brain-injury; or a disease, disorder or condition caused by prion.

Metal-DFO complexes as used according to the method and composition of the present invention may be prepared utilizing any technology or procedure known in the art, e.g., as described in International Publication No. WO2011021203. Possible procedures for the preparation of Zn-DFO and Ga-DFO complexes having various Zn-DFO/Ga-DFO stoichiometric ratios are provided hereinbelow. Such complexes having other stoichiometric ratios may be prepared using similar procedures.

A Zn-DFO complex having Zn:DFO stoichiometric ratio of 1.0:1.0 may be prepared, e.g., by mixing 10 mM solution of DFO with an equal volume of 10 mM $ZnCl_2$ solution, titrating to a pH between 5.0 to 7.5, heating the mixture to 45° C. for 30 min, and cooling down. Alternatively, such a complex may be prepared by drying the contents of 1 vial (500 mg, 0.76 mmole) of Desferal®, by adding 168 mg of dry zinc acetate anhydrous (0.76 mmole), adding double distilled water until the contents fully dissolve (about 10 ml), warming the solution to 40° C. for 45 minutes, and cooling down.

A Zn-DFO complex having Zn:DFO stoichiometric ratio of 1.25:1.0 may be prepared, e.g., by mixing 10 mM solution of DFO with an equal volume of 6 mM $ZnCl_2$ solution, titrating to a pH between 5.0 to 7.5, heating to 45° C. for 30 min, and cooling down.

A Zn-DFO complex having Zn:DFO stoichiometric ratio of 0.6:1.0 may be prepared, e.g., by mixing 10 mM DFO solution with an equal volume of 12.5 mM $ZnCl_2$ solution and 10 ml of 5.5 mM histidine, titrating to a pH between 5.0 to 7.5, heating to 45° C. for 30 min, and cooling down.

A Zn-DFO complex having Zn:DFO stoichiometric ratio of 0.2:1.0 may be prepared, e.g., by mixing 50 mM DFO solution with ⅕ the volume of 50 mM $ZnSO_4$ solution, titrating to a pH between 5.0 to 7.5, heating to 40° C. for 45 min, and cooling down.

A Ga-DFO complex having Ga:DFO stoichiometric ratio of 1.0:1.0 may be prepared, e.g., by mixing 10 mM solution of DFO with an equal volume of 10 mM $GaCl_3$ solution, titrating to pH of about 5.0 (using HCl) and then to a pH between 5.0 to 7.5 (using NaOH), at room temperature. A similar complex having Ga:DFO stoichiometric ratio of 0.6:1.0 may be prepared, e.g., by mixing 5 mM DFO solution with an equal volume of 3 mM $GaCl_3$ solution, at room temperature, titrating to a pH between 5.0 to 7.5.

In still another aspect, the present invention relates to a metal-DFO complex or a combination thereof for use in preventing, inhibiting, reducing, or ameliorating neurodegeneration, thus more particularly treating a disease, disorder or condition characterized by or associated with neurodegeneration.

In yet another aspect, the present invention relates to use of a metal-DFO complex or a combination thereof in the preparation of a pharmaceutical composition for preventing, inhibiting, reducing, or ameliorating neurodegeneration, thus more particularly treating a disease, disorder or condition characterized by or associated with neurodegeneration.

As previously shown, DFO is capable of abstracting metals such as Fe and Zn from human plasma in vitro (Sooriyaarachchi and Gailer, 2010). It is thus postulated that under physiological conditions, administration of DFO and metal ions, e.g., Zn-, Ga-, Eu-, or Gd-ions, from two separate compositions, either concomitantly or sequentially (provided that the interval between administrations of the two components is determined such that at least a major amount of the component first administered is available in the circulation, i.e., not yet excreted, at the time the second component is administered), will result in the formation of a metal-DFO complex in situ.

In another aspect, the present invention thus relates to a method for preventing, inhibiting, reducing or ameliorating neurodegeneration, thus treating a disease, disorder or condition characterized by or associated with neurodegeneration, in a subject in need thereof, comprising administering to said subject therapeutically effective amounts of DFO or a pharmaceutically acceptable salt thereof, and ions of at least one, i.e., one, two, three or more, metal, wherein said DFO or pharmaceutically acceptable salt thereof and said metal ions are administered from two separate compositions either concomitantly or sequentially at any order and within a time period not exceeding 6 hours, so as to obtain in situ a complex of said DFO and said at least one metal.

In a further aspect, the present invention thus provides a kit comprising (i) a first pharmaceutical composition comprising DFO or a pharmaceutically acceptable salt thereof; (ii) a second pharmaceutical composition comprising ions of at least one metal; and (iii) instructions to administer said compositions, either concomitantly or sequentially at any order and within a time period not exceeding 6 hours, so as to obtain in situ a complex of said DFO and said at least one metal to thereby prevent, inhibit, reduce, or ameliorate neurodegeneration, and consequently treat a disease, disorder or condition characterized by, or associated with, neurodegeneration.

In certain embodiments, the first pharmaceutical composition comprised within the kit of the present invention comprises DFO. In other embodiments, said first pharmaceutical composition comprises a DFO salt. Examples of pharmaceutically acceptable salts of DFO include, without limiting, the mesylate salt, the esylate salt, the tosylate salt, the sulfate salt, the sulfonate salt, the phosphate salt, the carboxylate salt, the maleate salt, the fumarate salt, the tartrate salt, the benzoate salt, the acetate salt, the hydrochloride salt, and the hydrobromide salt, wherein the mesylate salt is preferred.

In certain embodiments, the second pharmaceutical composition comprised within the kit of the present invention comprises ions of zinc, gallium, indium, silver, cobalt, gold, a lanthanide such as those listed above, or a combination thereof. In certain embodiments, said second pharmaceutical composition comprises ions of more than one metal, e.g., ions of two or three metals, in any quantitative ratios. For example, a composition comprising a ions of two metals may contain said two metals in a quantitative ratio of about 100:1 to about 1:100, e.g., in a quantitative ratio of about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100.

In particular embodiments, the second pharmaceutical composition comprised within the kit of the invention comprises ions of Zn, Ga, Eu, Gd, or any combination thereof. In more particular such embodiments, said second composition comprises ions of both Zn and Ga, e.g., wherein the quantitative ratio of the Zn ions to the Ga ions is in a range of about 100:1 to about 1:100, e.g., about 20:1 to about 1:20, about 10:1 to about 1:10, about 4:1 to about 1:4, about 3:1 to about 1:3, about 2:1 to about 1:2, or about 1:1. Certain such compositions are those wherein the amount of the Zn ions is higher than that of the Ga ions, e.g., wherein the quantitative ratio of the Zn ions to the Ga ions in the composition is in a range of about 10:1 to about 2:1, e.g., about 10:1, about 9:1, about 8:1, about 7:1, about 6:1, about 5:1, about 4:1, about 3:1, or about 2:1.

In certain embodiments, the second pharmaceutical composition comprised within the kit of the invention comprises ions of three or more metals, e.g., ions of Zn, Ga and one or more additional metals such as, e.g., Eu or Gd.

The metal ions comprised within the second pharmaceutical composition may be in the form of cations (salts) in any possible valence state (depending on the specific metal), or in complexes with organic compounds such as aromatic and non-aromatic compounds having a heteroatom-containing moiety, e.g., carbonyl compounds, hydroxy compounds, heterocyclic compounds, alkenes and alkynes (metals form complexes with double and triple bonds). Non-limiting examples of ligands (mono-, bi-, tridentate-, etc.) forming metal complexes are acetate, gluconate, acetylacetone, stearate, ricinoleate, tris(2-aminoethyl)amine, crown ethers, porphyrins, alkyl phosphates such as dialkyldithiophosphate, and heterocycles such as terpyridine, pyrithione and metalloocenes.

For example, zinc ions may be present in the form of a zinc salt, e.g., $ZnCl_2$, or in complexes such as zinc acetate, zinc stearate, zinc crown ether, zn-porphyrin/crown ether conjugate, zinc protoporphyrin, zinc chlorophyll and bacteriochlorophyll, monomeric zinc dialkyldithiophosphate, zinc acetylacetone (trimer; $Zn_3(AcAc)_6$), zinc terpyridine (tridentate; $[Zn(Terpy)Cl_2]$) zinc tris(2-aminoethyl)amine carbonic anhydrase (Zn metalloenzyme), glutamate carboxypeptidase 11 (Zn metalloenzyme), organozinc compounds such as diethylzinc (I) and decamethyldizincocene (II) Zinc gluconate, Zinc pyrithione, and zinc ricinoleate. Galium ions may be present in the form of a galium salt, e.g., $GaCl_3$.

In certain embodiments, the first and second pharmaceutical compositions comprised within the kit of the present invention are administered concomitantly. In other embodiments, said compositions are administered sequentially, at any order, wherein the two administrations are carried out within a time period of up to 1 hour, 2 hours, 3 hours, 4 hours, 5 hours, or 6 hours.

Following the administration of the compositions comprised within the kit of the invention to a subject in need thereof, at least one metal-DFO complex is obtained in situ, which inhibits, reduces or ameliorates neurodegeneration, and consequently treats a disease, disorder or condition characterized by, or associated with, neurodegeneration in said subject.

The pharmaceutical compositions comprised within the kit of the present invention can be formulated, each independently, for any suitable route of administration, e.g., intravenous, intraarterial, intramuscular, intraperitoneal, intrathecal, epidural, intracerebral, intracerebroventricular, intrapleural, intratracheal or subcutaneous, administration; oral administration; rectal administration; nasal administration; or inhalation. It should thus be appreciated that the two compositions comprised within the kit of the invention may be administered using the same or different administration routes. Some administration routes, e.g., intraperitoneal or rectal, can be intended for treatment of intestinal malfunction linked to neurodegenerative diseases.

The kit disclosed herein is particularly advantageous when the DFO and the metal ions are preferably administered in different dosage forms, e.g., wherein one of said components is preferably administered orally and the other component is preferably administered parenterally, or at different dosage intervals; or when titration of one of said components, prior to administration, is desired by the prescribing practitioner.

The kit disclosed herein may thus comprise each one of the compositions in a ready for use form, e.g., formulated as a liquid for topical, nasal or oral administration, or may alternatively include one or both of the compositions as a solid composition that can be reconstituted with a solvent to provide a liquid oral dosage form. In cases one or both of the compositions are provided in a solid form for reconstitution with a solvent, the kit may further include a reconstituting solvent and instructions for dissolving said solid composition in said solvent prior to administration. Such a solvent should be pharmaceutically acceptable and may be, e.g., water, an aqueous liquid such as phosphate buffered saline (PBS), a non-aqueous liquid, or a combination of aqueous and non-aqueous liquids. Suitable non-aqueous liquids include, but are not limited to, oils, alcohols such as ethanol, glycerin, and glycols such as polyethylene glycol and propylene glycol.

Unless otherwise indicated, all numbers expressing quantities of ingredients and so forth used in the present description and claims are to be understood as being modified in all instances by the term "about". Accordingly, unless indicated to the contrary, the numerical parameters set forth in this specification and attached claims are approximations that may vary by up to plus or minus 10% depending upon the desired properties sought to be obtained by the present invention.

The invention will now be illustrated by the following non-limiting Examples.

EXAMPLES

Study 1. Blood-Brain Barrier (BBB) Penetration

In this study, the ability of the Zn-DFO complex to infiltrate into the brain was examined. Rats were injected intraperitoneally (IP) with increasing amounts of DFO alone or Zn-DFO complex, and the concentration of DFO was measured in their brains, thus monitoring their infiltrability.

In particular, male Sprague-Dawley (SD) rats (300 g average body weight, 3 animals per group) were injected IP with DFO (250, 500, or 1000 mg/kg body weight). For comparison, Zn-DFO solution in freshly prepared saline was injected IP (250, 500, or 1000 mg/kg body weight, which are equivalent to 883, 442, or 221 mg DFO/kg body weight, respectively).

The behavior of the rats was monitored for 90 min following the injection. Then, the animals were euthanized using an injection of ketamine-xylazine, and their hearts, livers, left kidneys, and brains were excised and weighted. Brain samples (300 mg tissue) were homogenized in 3 ml Lysis buffer. Tissue homogenates were incubated at 110° C. for 5 min and centrifuged for 5 min at 14,500 relative centrifugal force (RCF). An equal volume of 40% trichloroacetic acid (TCA) solution was added, forming a solution containing 20% TCA, which was vortexed and centrifuged again. The supernatants were transferred into cuvettes, and DFO concentration was spectrophotometrically measured, after addition of 10 mM of ferric iron solution (as a weak complex of iron, ferric-nitrilo-tri-acetate, at pH=7.4), and scanning the range of $\lambda$=380-580 nm. The final concentration was calculated according to the Beer-Lambert law, using $\varepsilon_{DFO}$=2460 $M^{-1}cm^{-1}$; the total amount of DFO per gram tissue and per whole brain were calculated. The results obtained are summarized in Table 1.

TABLE 1

Comparative study of the infiltrability of Zn-DFO and DFO into the rat brain

|  | Amount | DFO (mg/g organ) | DFO (mg/whole organ) | DFO infiltrated the brain (%) |
|---|---|---|---|---|
| Zn-DFO | 1000 mg/kg | 0.072 ± 0.011 | 0.133 ± 0.010 | 0.014% |
|  | 500 mg/kg | 0.031 ± 0.001 | 0.054 ± 0.002 | 0.012% |
|  | 250 mg/kg | 0.017 ± 0.002 | 0.032 ± 0.004 | 0.014% |
| DFO | 1000 mg/kg | 0.008 ± 0.004 | 0.019 ± 0.008 | 0.002% |
|  | 500 mg/kg | <0.005 | <0.005 | <0.0015% |
|  | 250 mg/kg | <0.005 | <0.005 | <0.0015% |

* The results are shown as average ± standard error.
† The OD was below the detection limit of the instrument (<0.005)

Fifteen min after the administration of 1000 mg/kg Zn-DFO complex, the rats looked passive and apathetic; however, no changes in the rats' behavior could be identified after injection of either 500 mg/kg or 250 mg/kg of Zn-DFO complex. Following injection of DFO alone, for the three doses, no changes in rats' behavior was observed.

The total amount of DFO found in the brain (mg/g), at the end of the experiments, was calculated for all groups—3 administered with DFO alone (250, 500 and 1000 mg/kg) and 3 administered with Zn-DFO (250, 500 and 1000 mg/kg). The fraction of DFO that had infiltrated into the brain remained nearly constant for the 3 doses of Zn-DFO, with an average of 0.0133%. For the corresponding doses of DFO alone, the value was 0.002% or less (due to the limited sensitivity of the instrument). Thus, the infiltrability of the Zn-DFO complex into the brain is at least 8.6-fold higher than that for the DFO alone, indicating that the Zn-DFO complex infiltrates into the brain markedly better than the DFO alone.

Study 2. Spinal Cord Injury

In this study, the therapeutic effect of metal-DFO complex on spinal cord injury was tested, using a contusion spinal cord injury model in C57BL/6 mice.

A contusion spinal cord injury model was employed using Infinite Horizon spinal cord impactor. The injury was performed at force setting of 70 kilodyne, for 100 ms (milisecond) on exposed T12 vertebra of the mouse (8 weeks old male), anesthetized with a ketamine-xylazine mixture (85: 15), and immobilized. Immediately before the impact, the mice were injected with buprenorphine (0.1 mg/ml/kg body weight) as an analgesic.

Twenty one mice, after contusion, were divided into three groups (n=7), according to their treatment as following (Basso et al., 2006): Group 1—control untreated; Group 2—treated with saline (IP injections of 100 µl on Days 1, 2, 3, 4, 6, 8, 10, 12, 14, 17, 20, 23, 27, 31, 35, 39, and 42); Group 3—treated with Zn-DFO complex, 3 mg/kg body weight in saline (IP injections of 100 µl according to the same regimen as Group 2). Both treated groups (saline and Zn-DFO complex) received the first treatment 10 min following the Impactor-induced trauma.

The post-traumatic recovery of mice locomotion with or without treatment was assessed on a daily basis for the next 43 days, using open field Basso mouse scale (BMS) score as following: 0—no ankle movement; 1—slight ankle movement; 2—extensive ankle movement; 3—plantar placing of the paw with or without weight support, or occasional, frequent or consistent dorsal stepping but no plantar stepping; 4—occasional plantar stepping; 5—frequent or consistent plantar stepping, no coordination, or frequent or consistent plantar stepping, some coordination, paws rotated at initial contact and lift off (R/R); 6—frequent or consistent plantar stepping, some coordination, paws parallel at initial contact (P/R, P/P), or frequent or consistent plantar stepping, mostly coordinated, paws rotated at initial contact and lift off (R/R); 7—frequent or consistent plantar stepping, mostly coordinated, paws parallel at initial contact and rotated at lift off (P/R), or frequent or consistent plantar stepping, mostly coordinated, paws parallel at initial contact and lift off (P/P), and severe trunk instability; 8—frequent or consistent plantar stepping, mostly coordinated, paws parallel at initial contact and lift off (P/P), and mild trunk instability, or frequent or consistent plantar stepping, mostly coordinated, paws parallel at initial contact and lift off (P/P), and normal trunk stability and tail down or up & down; and 9—frequent or consistent plantar stepping, mostly coordinated, paws parallel at initial contact and lift off (P/P), and normal trunk stability and tail always up (P—parallel; R—rotated). The values were normalized considering the basal score on Day 0 as 100%.

On Day 43, the animals were euthanized, and their spinal cords were excised and stored in paraformaldehyde (PFA) 4% for histological analysis. Epon blocks were prepared, and the histological analysis was performed after staining with methylene blue.

Figure 1B:
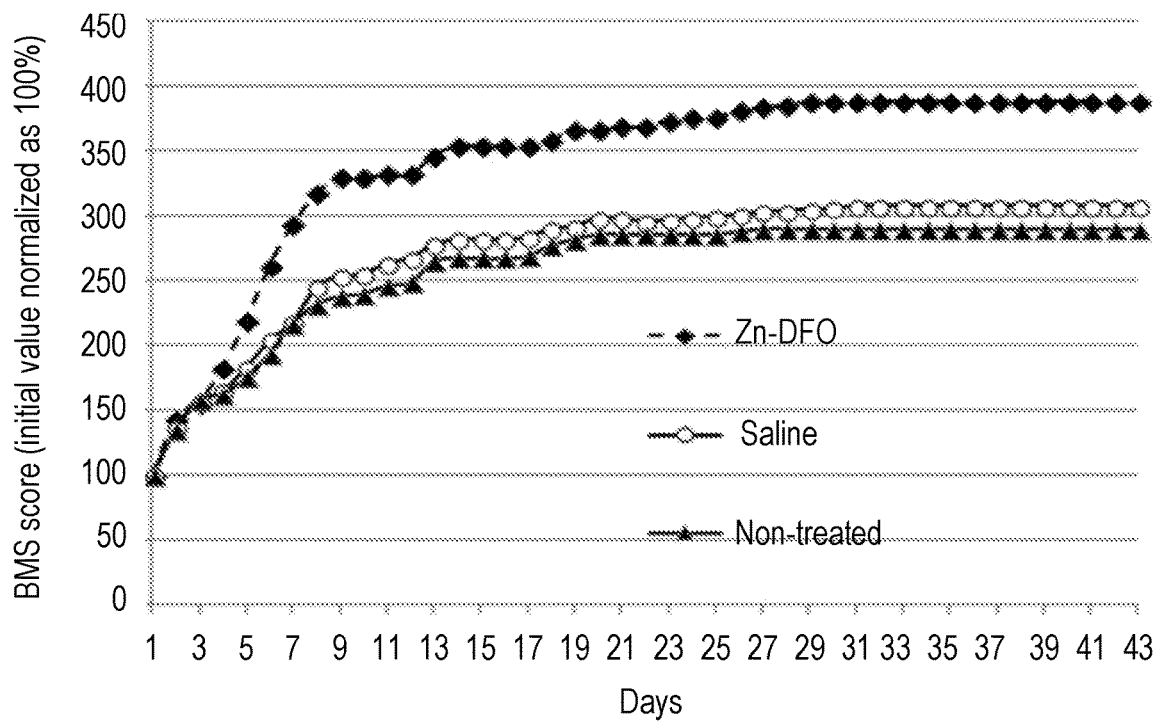

While comparing the BMS score of the post-traumatic recovery of the non-treated group with the saline-treated group, no statistically significant differences were found (FIG. 1). Both groups demonstrated limited rise of the BMS mobility score during the first 13 days, and then both groups reached a plateau at values of 265% (BMS Score=4.5) and 278% (BMS Score=4.8), respectively, from their initial scoring (Day 0). Mice treated with Zn-DFO demonstrated much faster improvement in the first two weeks, on Day 13 reaching 347% (BMS Score=5.1). The trend had been continued in the Zn-DFO-treated group through the next two weeks, reaching a plateau at 389% of their initial scoring on Day 29 (BMS score of 5.7/9.0).

Figure 2:
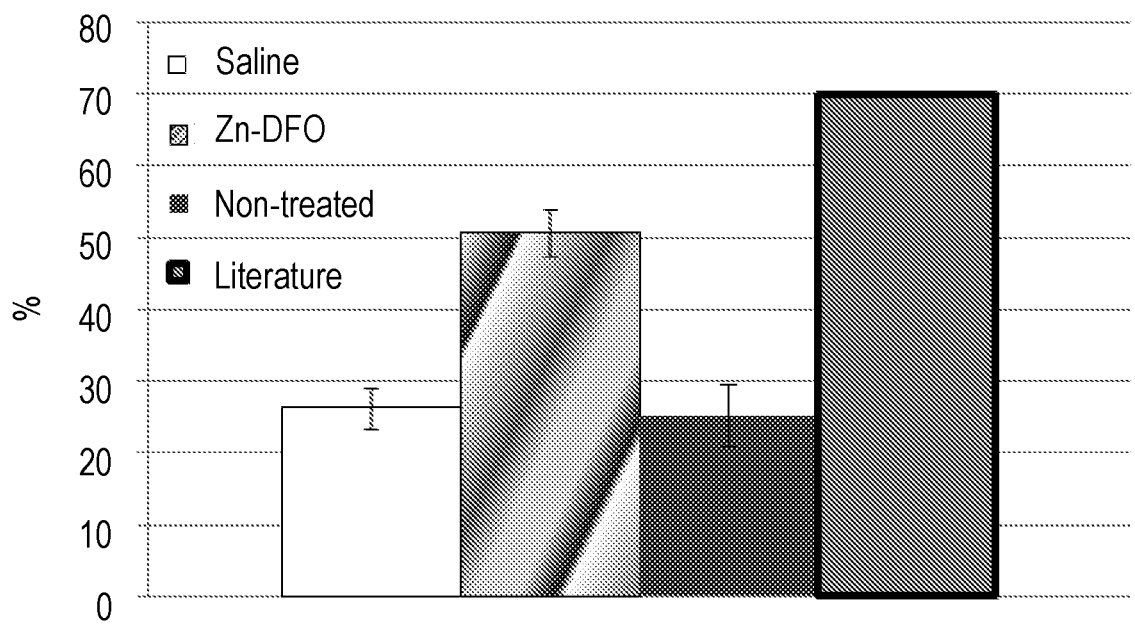
FIG. 2 shows white matter as a fraction (%) of the total area in mice after spinal cord injury, treated with Zn-DFO or saline. Values are shown as averages ±standard error.
Figure 3A:
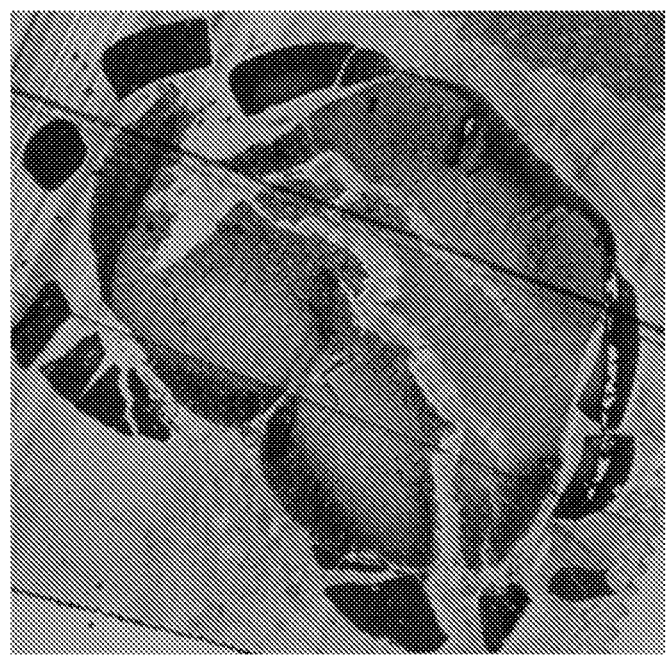
FIGS. 3A-3C show sections of the injured murine spinal cords treated with saline (3A) or Zn-DFO (3B), and without treatment (3C), stained with methylene blue. Pictures were taken at magnification of ×20.
Figure 3B:
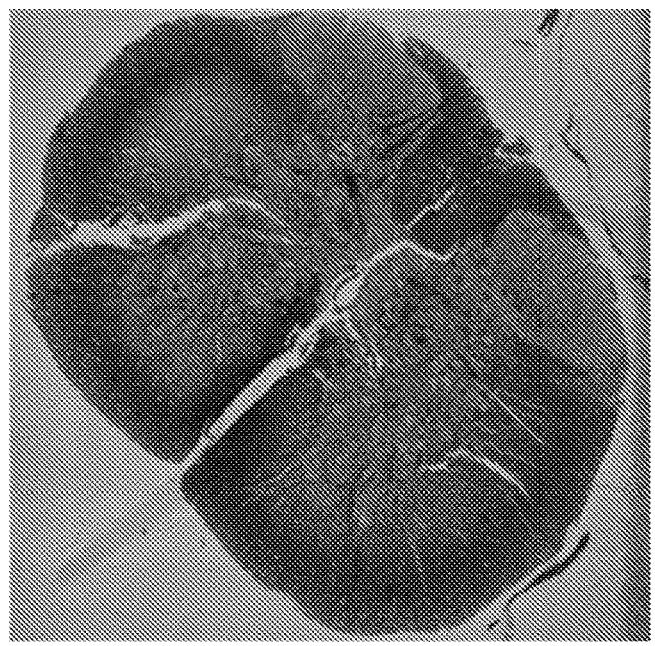
Figure 3C:
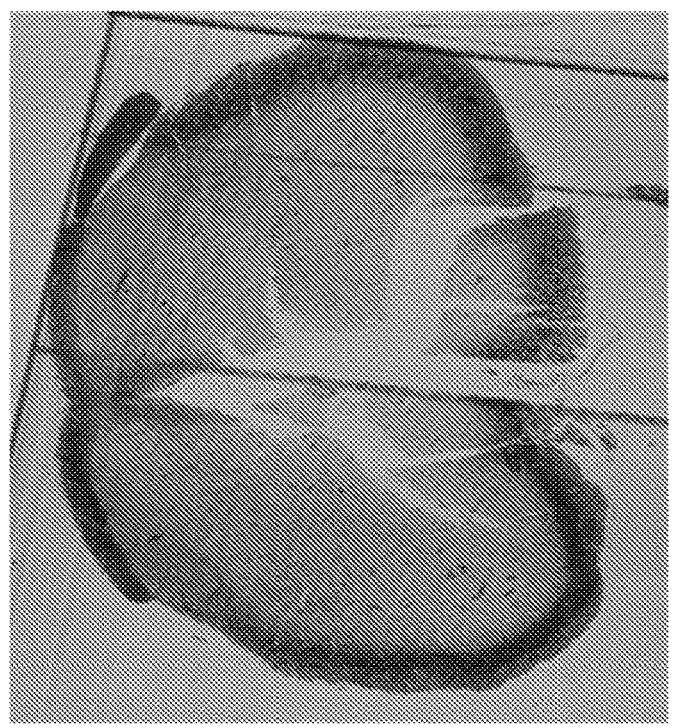

Consistent with the results of BMS recovery, the histological analysis showed lack of difference between the non-treated and saline-treated mice. Both of these groups demonstrated significant loss of the white matter from the value of 70% of the total area fraction (Cohen-Adad and Wheeler-Kingshott, 2014) to 26.3±2.9% and 25.3±4.2, respectively (FIG. 2), and reduced density of the grey matter. In addition, axonal retraction/dieback was observed in the gray matter of these groups. Treatment with Zn-DFO partly restored the normal morphology and arrangement of white and grey matter (white matter area of 50.8±3.3%) and their components (FIG. 2).

Figure 4A:
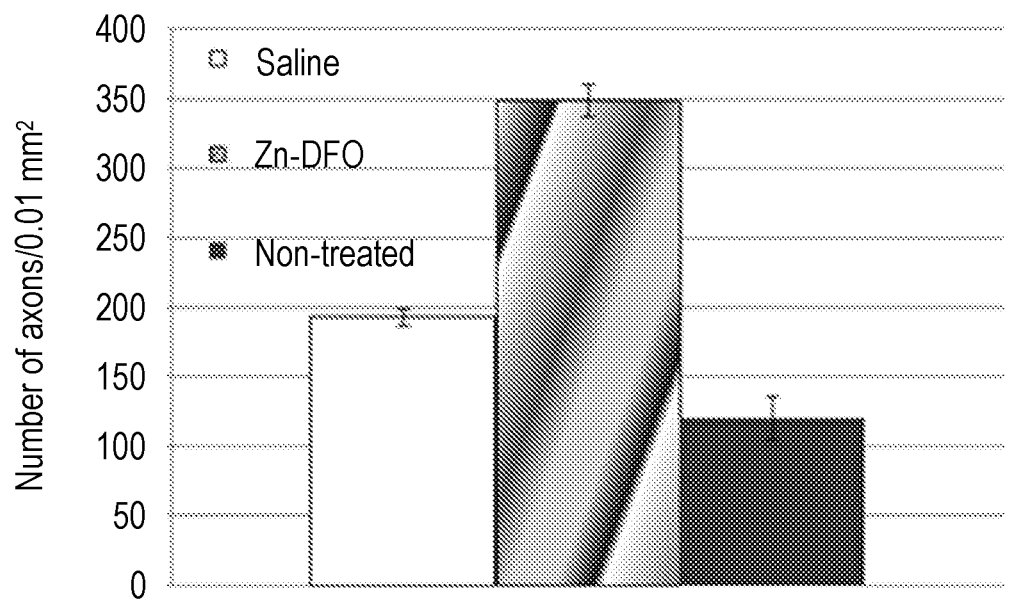
FIGS. 4A-4B show number of axons (4A) per 0.01 $mm^2$; and total myelin area (AU/0.01 $mm^2$) (4B) in spinal cord of mice after spinal cord injury, treated with Zn-DFO. Values are shown as averages ±standard error.
Figure 4B:
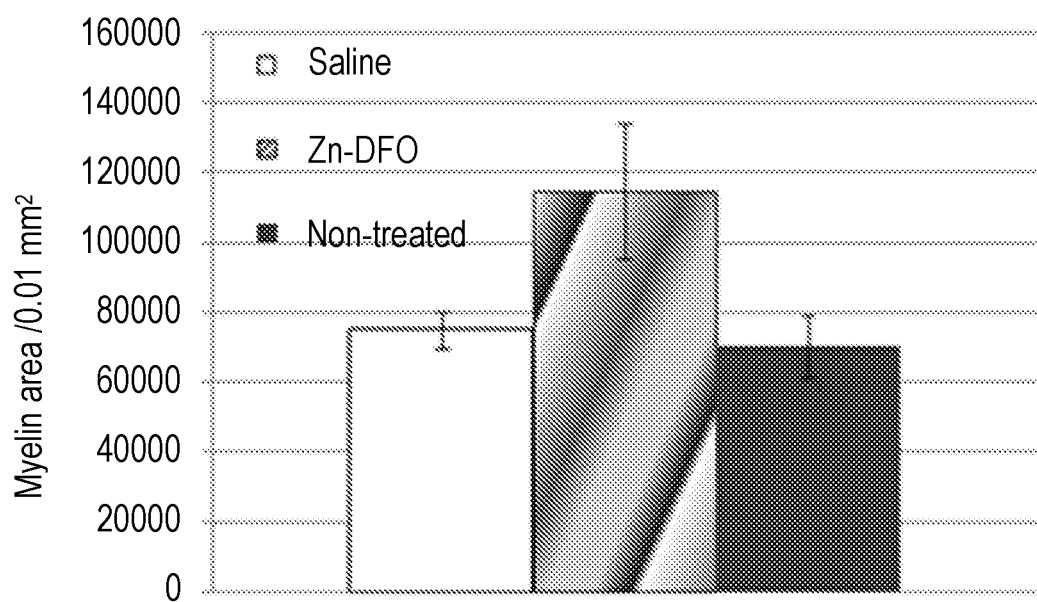

Spinal cord injury has an especially deteriorative effect on white matter of the studied animals, dwindling the number of axons per 0.01 mm$^2$ markedly below the reported value of 430±52 (Ward et al., 2014) and dramatically reducing the amount of structured myelin (FIGS. 4A-4B).

Figure 5A:
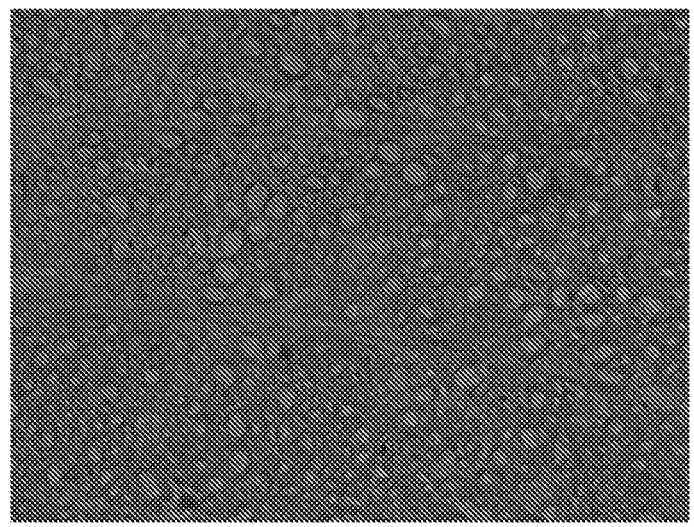
FIGS. 5A-5B show sections of the injured murine spinal cords treated with saline (5A) or Zn-DFO (5B), stained with H&E. Pictures were taken at magnification of ×60.
Figure 5B:
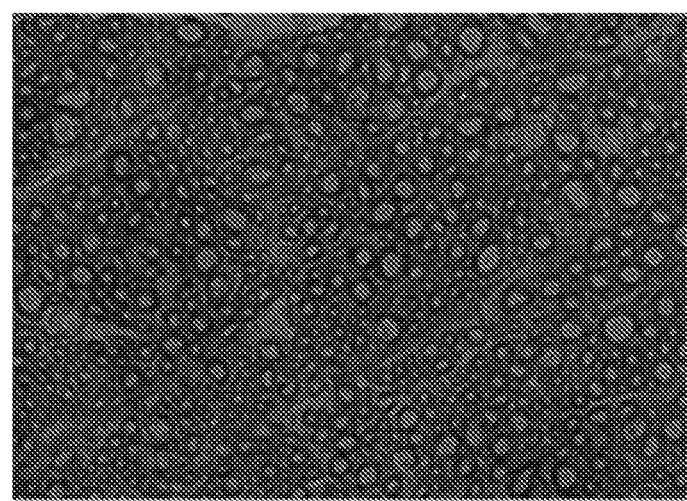

Treatment with saline limited the effect on the white matter components. In contrast, treatment with Zn-DFO proved markedly more efficacious (FIGS. 4-5), restoring the density of axons and axonal myelin sheath.

Figure 6:
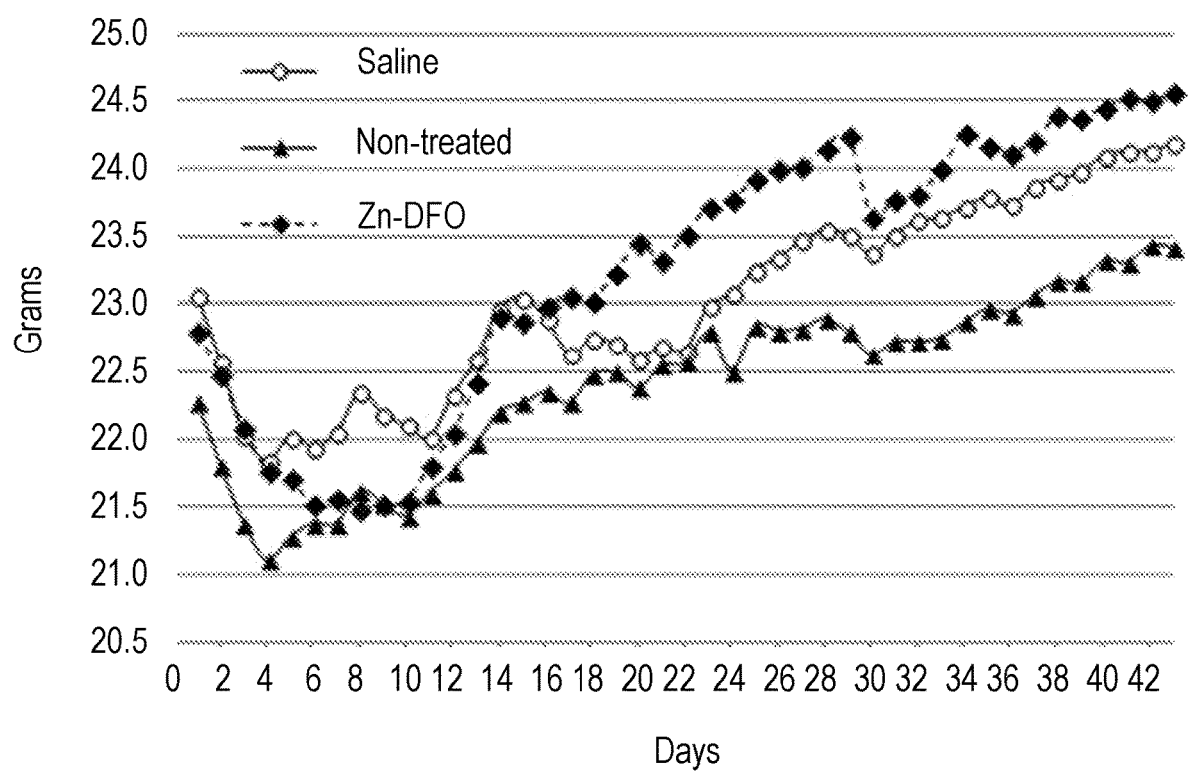
FIG. 6 shows recovery from spinal cord injury in mice treated with Zn-DFO—body weight. Values are shown as average.

Body weight measurements have shown that the animals treated with Zn-DFO gained weight better than the non-treated or saline-treated animals, demonstrating better post-traumatic recovery. However, treatment with saline had a somewhat beneficial effect when compared to untreated animals (FIG. 6).

Study 3. Experimental Autoimmune Encephalomyelitis—a Model for Multiple Sclerosis In this study, the therapeutic effect of metal-DFO complex on multiple sclerosis (MS) is tested, using the Experimental Autoimmune Encephalomyelitis (EAE) in mice.

EAE is induced in 8-week-old female C57BL/6 mice by subcutaneous (SC) injection of 125 µg of myelin oligodendrocyte glycoprotein 35-55 peptide (MOG$_{35-55}$) emulsified in complete Freund's adjuvant (CFA) containing 5 mg/ml heat-killed *Mycobacterium tuberculosis* into the left para-lumbar region. Immediately thereafter, and again at 48 h, the mice are inoculated intraperitoneal (IP) with 0.5 ml of pertussis toxin (400 ng). Seven days later, the mice are further challenged with an additional injection of MOG$_{35-55}$ peptide in CFA injected into the right para-lumbar region. Mice are treated with Zn-DFO or Ga-DFO daily as IP injections, 2 mg/kg and 6 mg/kg.

The severity of the disease is assessed using the scale shown in Table 2 (Bittner et al., 2014).

It is expected that mice exposed to MOG$_{35-55}$, without treatment, will develop the disease during 11-13 days after the first injection. The disease will aggravate during the next 3-4 days, reaching a peak value of the clinical signs score of 6-7 (see Table 2), and during the next two weeks, the condition of the animals will slightly improve, to clinical score of 5-6. The treatment with Zn-DFO or Ga-DFO, at 2 mg/kg is expected to delay the onset of the disease to Day 14, and the peak clinical score will be reached on Day 17, with a value of 4-5. During the next two weeks the score will improve to 3-4. The effects to be demonstrated by both compounds are expected to be similar to each other. The treatment with Ga-DFO 6 mg/kg is expected to postpone the onset of the disease to Day 15, and suppress its peak value (Day 19) to 3-4. The result of treatment with Zn-DFO, 6 mg/kg, the disease manifestations will be detected on Days 15-16 and the peak clinical score will be less than 3 (Day 19). The control group is not expected to express any clinical sign.

TABLE 2

Scale for assessing the severity of MS

| Grade | Clinical sign | Comments |
|---|---|---|
| 0 | No clinical signs | Normal gait, tail moves and can be raised, tail wraps around object if mouse is held at the base of the tail |
| 1 | Partially limp tail | Normal gait, tip of the tail droops |
| 2 | Paralyzed tail | Normal gait, tail droops |
| 3 | Hind limb paresis, uncoordinated movement | Uncoordinated gait, tail limps, hind limbs respond to pinching |
| 4 | One hind limb paralyzed | Uncoordinated gait with one hind limb dragging, tail limps, one hind limb does not respond to pinch |
| 5 | Both hind limbs paralyzed | Uncoordinated gait with both hind limbs dragging, tail limps, both hind limbs do not respond to pinch |
| 6 | Hind limbs paralyzed, weakness in forelimbs | Uncoordinated gait with forelimbs struggle to pull body, forelimbs reflex after pinching, tail limps |
| 7 | Hind limbs paralyzed, one forelimb paralyzed | Mouse cannot move, one forelimb responds to pinch, tail limps |
| 8 | Hind limbs paralyzed, both forelimbs paralyzed | Mouse cannot move, both forelimbs do not respond to pinch, tail limps |
| 9 | Moribund | No movement, altered breathing |
| 10 | Death | |

Study 4. MPTP Mouse Model of Parkinson's Disease

In this study, the therapeutic effect of metal-DFO complex on Parkinson's disease is tested, using the 1-methyl-4-phenyl-1,2,3,6-tetrahydropyridine (MPTP) model in mice.

Parkinson's disease is induced in 10 weeks old male C57BL/6 mice by four continuous IP injections of 20 mg/kg of MPTP, every 2 hours and during 8 hours, for 5 days (Jackson-Lewis and Przedborski, 2007). The animals are treated with Zn-DFO or Ga-DFO by daily IP injections, 2 mg/kg and 6 mg/kg, 30 min prior to the first exposure to MPTP. On day 8 the animals are euthanized. Immediately after the euthanasia, the striata are dissected out to perform biochemical and histological assessment of the damage to dopaminergic innervation.

It is expected that the exposure to MPTP will be manifested in the development of massive nigrostriatal dopamine neuron lesions. In the exposed and untreated mice the number tyrosine hydroxylase (TH)-positive neurons within the substantia nigra will be less than 40% of the control ones. Treatment with Zn-DFO or Ga-DFO 2 mg/kg is expected to result in restoration of this value to 65%. Administration of 6 mg/kg of either compound is expected to restore the number of TH-positive neurons to 85%-90% of the control value.

Additionally, MPTP is expected to diminish the brain level of dopamine to a level lower than the control by 10-12 fold. Treatment with either tested complex, or a combination thereof, is expected to markedly improve brain function and replenish brain dopamine levels, for administration of 2 mg/kg, and significantly better for 6 mg/kg.

Study 5. Streptozotocin-Induced Model of Alzheimer Disease

In this study, the therapeutic effect of metal-DFO complex on Alzheimer disease is tested, using the streptozotocin (STZ)-induced model in mice.

The disease is induced in 10 weeks old male C57BL/6 mice. The animals are placed into a stereotaxic frame for mice with nose and ear bars. STZ (3 mg/kg) or citrate buffer (for the control group) is injected bilaterally into the lateral ventricles at the following coordinates: AP—0.5 mm; ML ±1.1 mm; DV—2.8 mm relative to the bregma in a total volume of 1.5 µl to hemisphere. The injections are repeated 2 days after the first STZ injection (1.5 mg/kg). In order to confirm that the stereotaxic coordinates used throughout the study are suitable for STZ injection into lateral ventricles, FITC-labeled latex microspheres are injected into lateral ventricles and the presence of fluorescence in the surrounding brain tissue is examined 24 h after injection. Mice are treated with Zn-DFO or Ga-DFO daily, by IP injections of 2 mg/kg and 6 mg/kg, and with Eu-DFO as IP injection, 4 mg/kg. During 21 days of the experiment the mice undergo maze tests and novel object recognition (NOR) tests every 7 days. Clinical signs including general body condition and dehydration are monitored daily after the surgery. Every 7 days a representative number of mice is taken from each group and euthanized for Alzheimer's disease markers (amyloid-β protein, neurofilament expression, phosphorylation of Tau protein, synapsin expression) biochemical and histochemical evaluation (Ravelli et al., 2016).

It is expected that STZ injections will impair the outcomes of the maze and NOR tests. Zn-DFO and Ga-DFO complexes are expected to (largely) prevent this impairment in a dose-dependent manner, while the effect expected from Eu-DFO is similar to that of Ga-DFO. In addition, STZ injections are expected to increase in a time-dependent manner the expression of Aβ protein and the phosphorylation of Tau protein in the hippocampus. This process is expected to be inhibited by Zn-DFO and Ga-DFO in a dose-dependent manner. The effect of Eu-DFO complex is expected to be slightly better than Ga-DFO. The expression of synapsin is expected to continually diminish after the exposure to STZ. Zn-DFO and Ga-DFO are expected to attenuate this process dose-dependently. Only a minute effect of Eu-DFO is expected.

REFERENCES

Banin, E.; Morad, Y.; Berenshtein, E.; Obolenskt, A.; Yahalom, C.; Goldich, J.; Adibelli, F. M.; Zuniga, G.; DeAnda, M.; Pe'er J.; Chevion, M. Injury induced by chemical warfare agents: characterization and treatment of ocular tissues exposed to nitrogen mustard. *Invest Ophthalmol Vis Sci.* 2003, 44(7), 2966-2972

Basso, D. M.; Fischer, L. C.; Anderson, A. J.; Jakeman, L. B.; McTigue, D. M.; Popovich, P. G. Basso Mouse Scale for locomotion detects differences in recovery after spinal cord injury in five common mouse strains. *J Neurotrauma.* 2006, 23(5), 635-659

Bibi, H.; Vinokur, V.; Waisman, D.; Elenberg, Y.; Landesberg, A.; Faingersh, A.; Yadid, M.; Brod, V.; Pesin, J.; Berenshtein, E.; Eliashar, R.; Chevion, M. Zn/Ga-DFO iron-chelating complex attenuates the inflammatory process in a mouse model of asthma. *Redox Biol.* 2014, 2, 814-819

Bittner, S.; Afzali, A. M.; Wiendl, H.; Meuth, S. G. Myelin oligodendrocyte glycoprotein (MOG35-55) induced experimental autoimmune encephalomyelitis (EAE) in C57BL/6 mice. *J Vis Exp.* 2014, 86

Chevion, M. A site-specific mechanism for free radical induced biological damage: the essential role of redox-active transition metals. *Free Radic Biol Med.* 1988, 5(1), 27-37

Chevion, M. Protection against free radical-induced and transition metal-mediated damage: the use of "pull" and "push" mechanisms. *Free Radic Res Commun.* 1991, 12-13, 691-696

Chevion, M.; Jiang, Y.; Har-El, R.; Berenshtein, E.; Uretzky, G.; Kitrossky, N. Copper and iron are mobilized following myocardial ischemia: possible predictive criteria for tissue injury. *Proc Natl Acad Sci USA* 1993, 90(3), 1102-1106

Chevion, M.; Berenshtein, E.; Zhu, B-Z. The role of transition metal ions in free radical-mediated damage. *In: Reactive oxygen species in biological systems: an interdisciplinary approach, Colton and Gilbert (Eds.)*, 1998, Plenum Press, New York, pp 103-131

Cohen-Adad, J.; Wheeler-Kingshott, C. Quantitative MRI of the Spinal Cord, *Academic Press*, 2014, p 196

Connor, J. R.; Menzies, S. L.; Burdo, J. R.; Boyer, P. J. Iron and iron management proteins in neurobiology. *Pediatr Neurol.* 2001, 25(2), 118-129

Faden, A. I.; Wu, J.; Stoica B. A.; Loane, D. J. Progressive inflammation-mediated neurodegeneration after traumatic brain or spinal cord injury. *Br J Pharmacol.* 2016 173(4), 681-691

Jackson-Lewis, V.; Przedborski, S. Protocol for the MPTP mouse model of Parkinson's disease. *Nat Protoc.* 2007, 2(1), 141-151

Kim, N. H.; Park, S. J.; Jin, J. K.; Kwon, M. S.; Choi E. K.; Carp, R. I.; Kim Y. S. Increased ferric iron content and iron-induced oxidative stress in the brains of scrapie-infected mice. *Brain Res.* 2000, 884(1-2), 98-103

Kumar, V.; Gill, K. D. Aluminium neurotoxicity: neurobehavioural and oxidative aspects. *Arch Toxicol.* 2009, 83(11), 965-978

Mantyh, P. W.; Ghilardi, J. R.; Rogers, S.; DeMaster, E.; Allen, C. J.; Stimson, E. R., Maggio, J. E., Aluminum, iron, and zinc ions promote aggregation of physiological concentrations of beta-amyloid peptide. *J Neurochem.* 1993, 61(3), 1171-1174

Morad, Y.; Banin, E.; Averbukh, E.; Berenshtein, E.; Obolensky, A.; Chevion, M. Treatment of ocular tissues exposed to nitrogen mustard: beneficial effect of zinc desferrioxamine combined with steroids. *Invest Ophthalmol Vis Sci.* 2005, 46(5), 1640-1646

Orcutt, K. M.; Jones, W. S.; McDonald, A.; Schrock, D.; Wallace, K. J. A lanthanide-based chemosensor for bioavailable $Fe^{3+}$ using a fluorescent siderophore: an assay displacement approach. *Sensors* 2010, 10(2), 1326-1337

Ravelli, K. G.; Rosario, B. D.; Camarini, R.; Hernandes, M. S.; Britto, L. R. Intracerebroventricular Streptozotocin as a Model of Alzheimer's Disease: Neurochemical and Behavioral Characterization in Mice. *Neurotox Res.* 2016

Rouault, T. Iron metabolism in the CNS: implications for neurodegenerative diseases. *Nature Reviews Neuroscience* 2011 14, 551-564

Scheiber, I. F.; Mercer, J. F.; Dringen, R. Metabolism and functions of copper in brain. *Prog Neurobiol.* 2014, 116, 33-57

Siganos, C. S.; Frucht-Pery, J.; Muallem, M. S.; Berenshtein, E.; Naoumidi, I.; Ever-Hadani, P.; Pallikaris I. G.; Siganos D. S.; Chevion, M. Topical use of zinc desferrioxamine for corneal alkali injury in a rabbit model. *Cornea* 1998, 17(2), 191-195

Singh, N.; Haldar, S.; Tripathy, A. K.; McElwee, M. K.; Horback, K.; Beserra, A.

Iron in neurodegenerative disorders of protein misfolding: a case of prion disorders and Parkinson's disease. *Antioxid Redox Signal* 2014 21(3), 471-484

Sooriyaarachchi, M.; Gailer, J. Removal of $Fe^{3+}$ and $Zn^{2+}$ from plasma metalloproteins by iron chelating therapeutics depicted with SEC-ICP-AES. *Dalton Trans.* 2010, 39(32), 7466-7473

Wan, W.; Cao, L.; Kalionis, B.; Xia, S.; Tai, X. Applications of Induced Pluripotent Stem Cells in Studying the Neurodegenerative Diseases. *Stem Cells Int.* 2015, 2015, 382530

Ward, R. E.; Huang, W.; Kostusiak, M.; Pallier, P. N.; Michael-Titus, A. T.; Priestley, J. V. A characterization of white matter pathology following spinal cord compression injury in the rat. *Neuroscience.* 2014, 260, 227-239

Williams, T. L.; Urbanc, B.; Marshal, K. E.; Vadukul, D. M.; Jenkins, A. T.; Serpell, L. C. Europium as an inhibitor of Amyloid-β(1-42) induced membrane permeation. *FEBS Lett.* 2015, 589(21), 3228-3236

The invention claimed is:

1. A method for inhibiting, reducing or ameliorating neurodegeneration associated with the brain or the spinal cord in a subject in need thereof, the method comprising:
    administering to said subject a therapeutically effective amount of zinc-desferrioxamine B complex,
    wherein the subject suffers from a neurodegenerative disease, disorder or condition associated with the brain or spinal cord, and said neurodegenerative disease, disorder or condition is Parkinson's disease, Alzheimer's disease, amyotrophic lateral sclerosis, Huntington's disease, or age-related brain degeneration.

2. The method of claim 1, comprising administering a combination of Zn-DFO complex and Ga-DFO complex, wherein the quantitative ratio of said Zn-DFO complex to said Ga-DFO complex in said combination is in a range of 100:1 to 1:100.

3. The method of claim 1, comprising administering a combination of Zn-DFO complex, Ga-DFO complex, and at least one additional metal-DFO complex.

4. The method of claim 1, wherein said subject suffers from a disease, disorder or condition caused by a prion.

5. The method of claim 4, wherein said disease, disorder or condition caused by the prion is Creutzfeldt-Jakob disease or a subtype thereof, Gerstmann-Sträussler-Scheinker syndrome, fatal familial insomnia, kuru, Familial spongiform encephalopathy, or multiple system atrophy.

* * * * *